United States Patent
Bardonnet et al.

(10) Patent No.: US 9,981,062 B2
(45) Date of Patent: May 29, 2018

(54) METHOD FOR PRODUCING A BONE PASTE

(71) Applicant: BIOBANK, Presles en Brie (FR)

(72) Inventors: Raphael Bardonnet, Seine-Port (FR); Ana Barbeito, Paris (FR)

(73) Assignee: BIOBANK, Presies en Brie (FR)

( * ) Notice: Subject to any disclaimer, the term of this patent is extended or adjusted under 35 U.S.C. 154(b) by 0 days. days.

(21) Appl. No.: 15/305,302

(22) PCT Filed: Apr. 21, 2015

(86) PCT No.: PCT/FR2015/051076
§ 371 (c)(1),
(2) Date: Oct. 19, 2016

(87) PCT Pub. No.: WO2015/162372
PCT Pub. Date: Oct. 29, 2015

(65) Prior Publication Data
US 2017/0035936 A1 Feb. 9, 2017

(30) Foreign Application Priority Data
Apr. 25, 2014 (FR) .................................. 14 53726

(51) Int. Cl.
| A61L 27/32 | (2006.01) |
| A61L 27/36 | (2006.01) |
| A61L 27/46 | (2006.01) |
| A61L 27/22 | (2006.01) |

(52) U.S. Cl.
CPC ......... *A61L 27/3608* (2013.01); *A61L 27/222* (2013.01); *A61L 27/365* (2013.01); *A61L 27/3683* (2013.01); *A61L 27/46* (2013.01); *A61L 2430/02* (2013.01)

(58) Field of Classification Search
None
See application file for complete search history.

(56) References Cited

U.S. PATENT DOCUMENTS

| 5,997,544 A * | 12/1999 | Nies ................... A61B 17/8802 606/92 |
| 6,576,015 B2 * | 6/2003 | Geistlich ................... A61F 2/28 424/422 |
| 6,576,249 B1 * | 6/2003 | Gendler ................. A61K 35/32 424/422 |
| 8,613,938 B2 * | 12/2013 | Akella ................ A61L 24/0063 424/400 |
| 2002/0018796 A1 * | 2/2002 | Wironen ................... A61F 2/28 424/423 |
| 2002/0076429 A1 * | 6/2002 | Wironen ................... A61F 2/28 424/426 |
| 2007/0202190 A1 * | 8/2007 | Borden .................. A61K 35/32 424/549 |
| 2008/0014279 A1 * | 1/2008 | Talton .................. A61K 9/0024 424/489 |
| 2016/0000971 A1 * | 1/2016 | Giorno .................... A61L 27/40 424/423 |

FOREIGN PATENT DOCUMENTS

| EP | 1341545 | 9/2003 |
| WO | WO-99/38543 A1 | 8/1999 |

OTHER PUBLICATIONS

International Search Report for related International Application No. PCT/FR2015/051076; dated Jul. 30, 2015.

* cited by examiner

*Primary Examiner* — Ralph J Gitomer
(74) *Attorney, Agent, or Firm* — Miller, Matthias & Hull LLP

(57) ABSTRACT

The invention relates to a method for preparing an osteoconductive bone paste by heating an initial mixture containing an aqueous solution and a granular material including collagen and minerals. A portion of the collagen and the minerals are contained in grains of bone matrix. The initial mixture is heated enough to transform a portion of the collagen into gelatine and thus to obtain a cohesive bone paste having a predefined viscosity.

22 Claims, 2 Drawing Sheets

500 μm

METHOD FOR PRODUCING A BONE PASTE

CROSS-REFERENCE TO RELATED APPLICATION

This Application is a 35 USC § 371 US National Stage filing of International Application No. PCT/FR2015/051076 filed on Apr. 21, 2015, and claims priority under the Paris Convention to French Patent Application No. 1453726 filed on Apr. 25, 2014.

FIELD OF THE DISCLOSURE

The invention relates to methods for the preparation of bone paste.

BACKGROUND OF THE DISCLOSURE

Document EP1341545 describes an example of such method, in which a mixture of demineralized bone and water is heated to obtain a pasty medium (viscous phase), which is then mixed with demineralized or non-demineralized bone (solid phase) to form a bone gel or bone putty. This method is complex because it first involves a step of preparing the viscous phase, and then there is the addition of the solid phase. The mixing must be carried out in a sterile environment enabling surgical use, which increases the complexity. In addition, this method has disadvantages, such as the bone paste obtained in this manner is generally inhomogeneous since there is discontinuity between the two phases.

Also known, from document US 2007/0202190, is a similar method that uses cortical bone as the raw material. A fraction of the raw material is subjected to heat treatment at less than 100° C. (without reaching, let alone exceeding, a boiling point) and acid treatment to extract gelatin and, after neutralization and drying, to form a mineralized gelatin. Another fraction of this raw material is distilled in the appropriate manner (typically by acid treatment followed by neutralization and drying) to form demineralized bone powder (DBM—Demineralized Bone Matrix). Bone paste obtained by this method is the result of mixing the mineralized gelatin, DBM, and a liquid phase, such that an osteoinductive effect is obtained. Concerns about injectability, typically via syringe, arise with this type of mixture, due to the presence of particles of different composition. Furthermore, as no terminal sterilization process can be applied to the final mixture, the sterility of the product (required for therapeutic use) requires working under sterile conditions, which makes this an expensive and complex method.

In addition, the preservation of osteoinductive proteins of the DBM fraction is a risk factor in terms of health because prions, which are proteins, are not eliminated during preparation and could be transmitted to the recipient patient. This is why the method disclosed by US 2007/0202190, which is complex with sensitive steps, is of limited use in practice.

Document US 2002/0076429 discloses a method consisting of obtaining a pasty medium (viscous phase) from dehydrated gelatin that has been heat treated (for example by autoclaving) in order to both sterilize it and increase its viscosity. The gelatin is then ground under sterile conditions and mixed with osteoconductive and/or osteoinductive product. The complete process involves grinding and mixing the osteoconductive and/or osteoinductive product in a sterile environment, which makes the method both complex and costly. In addition, the obtained product is solid at 37° C., and requires the surgeon to heat the product to soften it prior to implant, which makes the product complex to use.

SUMMARY OF THE DISCLOSURE

The present invention aims to overcome some or all of these disadvantages.

To this end, the invention provides a method for preparing an osteoconductive bone paste, comprising at least the following steps:
  (a) a providing step during which an initial mixture is supplied, in a container, including an aqueous solution and a granular product comprising at least collagen and minerals, the collagen representing between 30% and 90% of the granular product by dry weight and the minerals representing between 10% and 70% of the granular product by dry weight, at least a portion of the collagen being contained in particles of at least partially mineralized bone matrix,
  (b) a heating step during which the initial mixture is heated in the container at a temperature of at least 100° C., preferably 121° C., to transform a portion of the collagen into gelatin so that there is continuity between the gelatin and the at least partially mineralized bone matrix and a cohesive bone paste is obtained, the heating step enabling sterilization of the bone paste in the container, by means of which, after cooling and gelling, the bone paste is ready for use and remains sterile in the container, the container being in a closed and fluidtight state.

With these arrangements, a homogeneous bone paste is obtained that is ready for use, of a mixed composition (at least gelatin/demineralized bone matrix/mineralized bone matrix) which is favorable to osteoconduction, and that has good properties of malleability (bone paste is plastically deformable) and cohesion (this bone paste does not melt at 38° C.). These particularly advantageous properties are obtained because heating is applied to the whole mixture (in one step), thereby obtaining excellent continuity between the solid phase and the viscous phase (gelatin).

Heating at a temperature of about 121° C., or more generally greater than 100° C., transforms the constituents of the granular product (in particular with exudation of gelatin from the particles, in particular those already partially or fully demineralized) while having an advantageous sterilizing effect. The at least partially mineralized bone matrix particles are also transformed due to the heating, benefitting the rheology of the bone paste. Phase continuity between the gelatin, the demineralized fraction, and the mineralized fraction is obtained. It is understood that to obtain the pasty texture, it is unnecessary to add a binder during a mixing step which could be detrimental to the sterile state.

The bone paste reliably and simply obtained in this manner is osteoconductive, sterile, and ready to use. As the entire mixture is subjected to heat exceeding 100° C., typically by autoclaving, it is understood that the preservation of osteoinductive proteins is not the aim, the benefits of viral safety and sterility of the finished product being the primary intent. The finished product can be prepared in a fluidtight container, so that its composition is completely controlled and it can be directly injected if the fluidtight container is a syringe.

Note that in the present application, the term "mineralized bone matrix" is used to designate a bone matrix (bone tissue) which has not undergone any demineralization treatment and which comprises a mineral component (about 70% by dry weight) and a collagen component (about 30% by dry weight). The bone matrix may be of human or animal origin and may be of cortical, cancellous, or cortical-cancellous bone.

Note that in the present application, terms such as "granular" or "particle" are used to refer to any material formed of solid particles, fragments, or filaments of a size between 0 and a few millimeters.

Various embodiments of the method according to the invention may possibly also make use of one or more of the following arrangements:

- in the heating step (b), the initial mixture is heated for a period of between 10 minutes and 2 hours, preferably between 18 minutes and 1 hour;
- in the heating step (b), the initial mixture is heated at a temperature of between 50° C. and 200° C., for example between 100° C. and 200° C., preferably between 100° C. and 150° C.;
- in the heating step (b), the initial mixture is heated for a period of between 18 minutes and 1 hour and at a temperature of between 100° C. and 150° C.;
- in the providing step (a), the initial mixture is supplied in a container in a closed and fluidtight state, and it is heated in the heating step (b) in said container in this closed and fluidtight state; the term "fluidtight" here is understood to mean hermetically sealed against water vapor and micro-organisms to a differential pressure of at least 1 bar (in the following, the more concise expression "fluidtight container" will be used);
- in the providing step (a), the fluidtight container is placed in a sealed pouch and is heated in the heating step (b) in said sealed pouch: a fully packaged sterile bone paste is thus obtained that is ready for use;
- the heating step (b) is carried out at a sufficient temperature and for a sufficient period to sterilize the bone paste;
- the heating step (b) is carried out in water vapor, a water bath, or dry heat;
- in the providing step (a), the minerals represent between 20% and 60% by dry weight of the granular product and the collagen represents between 40 and 80% by dry weight of the granular product;
- in the providing step (a), the aqueous solution of the initial mixture is selected from among water, normal saline, or physiological buffer solution;
- in the providing step (a), the aqueous solution represents between 40% and 75% of the initial mixture by total weight;
- in the providing step (a), the granular material/product has a particle size of less than 4 mm, preferably less than 1.5 mm;
- in the providing step (a), the initial mixture further contains a mineralized osteoconductive biomaterial; this mineralized osteoconductive biomaterial may be of human or animal origin (deproteinized bone matrix) or synthetic (hydroxyapatite, tricalcium phosphate, bioglass, or other implantable material);
- in the providing step (a), the initial mixture contains completely demineralized bone matrix particles mainly comprising collagen, and mineralized bone matrix particles comprising collagen and minerals;
- in the providing step (a), the initial mixture contains partially demineralized bone matrix particles comprising between 20% and 70% minerals by dry weight, preferably between 40% and 60% minerals by dry weight;
- in the providing step (a), the initial mixture comprises purified collagen and mineralized bone matrix particles;
- the providing step (a) comprises at least the following sub-steps:
  - (a1) a sub-step of preparing completely demineralized bone matrix particles by demineralization and grinding of bone (the demineralization preceding or following the grinding),
  - (a2) a sub-step of preparing mineralized bone matrix particles by grinding bone,
  - (a3) a sub-step of mixing during which at least the completely demineralized bone matrix particles, the mineralized bone matrix particles, and the aqueous solution are mixed to obtain said initial mixture;
- the providing step (a) comprises at least the following sub-steps:
  - (a'1) a sub-step of preparing partially demineralized bone matrix particles by demineralization and grinding of bone (the demineralization preceding or following the grinding),
  - (a'3) a sub-step of mixing during which at least the partially demineralized bone matrix particles and the aqueous solution are mixed to obtain said initial mixture;
- the providing step (a) comprises at least the following sub-steps:
  - (a"2) a sub-step of preparing mineralized bone matrix particles by grinding bone,
  - (a"3) a sub-step of mixing during which at least the mineralized bone matrix particles, the purified collagen, and the aqueous solution are mixed to obtain said initial mixture.
- during the mixing sub-step (a3, a'3, or a"3), a mineralized osteoconductive biomaterial is mixed with the other constituents of the initial mixture;
- during the mixing sub-step (a3, a'3, or a"3), at least hyaluronic acid and/or its derivatives, in particular cross-linked hyaluronic acid, is mixed with the other constituents of the initial mixture.

BRIEF DESCRIPTION OF DRAWINGS

Other features and advantages of the invention will become apparent from the following description of one of its embodiments, given by way of non-limiting example, with reference to the accompanying drawing.

In the drawings.

DETAILED DESCRIPTION OF THE DISCLOSURE

Figure 1:
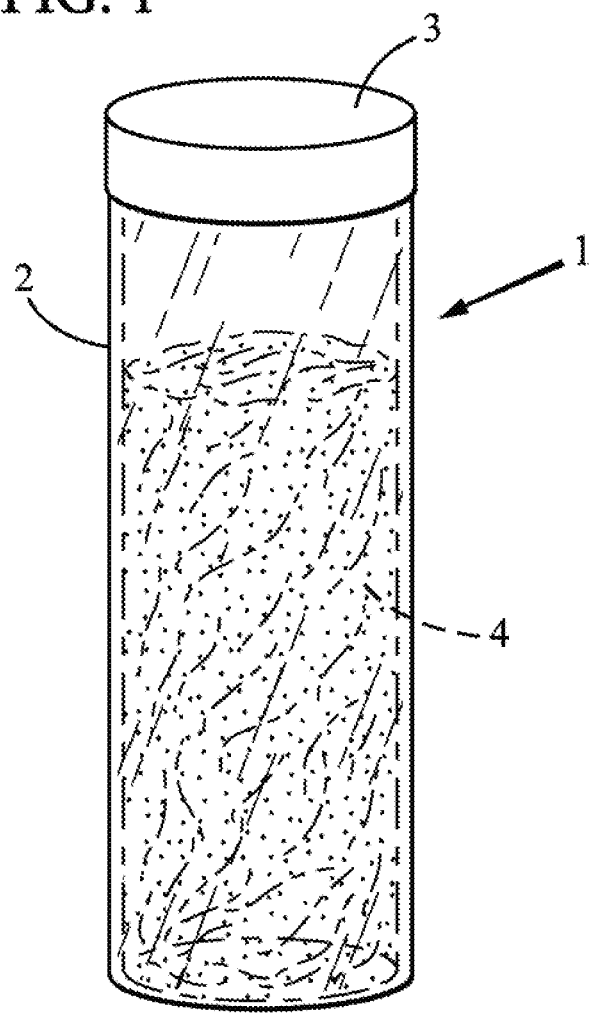
FIG. 1 represents a vial containing bone paste obtained by the method according to the invention.

The method of the invention allows preparing a malleable bone paste that can be used as bone filler in medical applications.

This bone paste can be prepared from a collagen fraction and a mineralized fraction. The collagen fraction is obtained from an at least partially demineralized bone matrix or from purified collagen. The mineralized fraction is obtained from bone tissue of human or animal origin, which is cortical, cancellous, or cortical-cancellous, referred to herein as mineralized bone matrix.

The method for preparing bone paste according to the invention comprises two major steps:
(a) providing an initial mixture containing an aqueous solution, a collagen fraction, and a mineralized fraction,
(b) heating.

(a) Step of Providing the Initial Mixture:

During this step (a), an initial mixture is provided that contains at least:
an aqueous solution, and
a granular product comprising at least collagen and minerals, at least a portion of the collagen being contained in at least partially mineralized bone matrix particles.

The collagen may originate from completely or partially demineralized bone matrix or from any other source of purified collagen.

The composition of the initial mixture may, for example, be as follows:
it may comprise completely demineralized bone matrix particles or purified collagen and mineralized bone matrix particles;
it may comprise partially demineralized bone matrix particles.

In the granular product of the initial mixture, collagen may represent between 30% and 90% by dry weight of the granular product (advantageously between 40% and 80%), and the minerals between 10% and 70% by dry weight of the granular product (advantageously between 20% and 60%).

The granular product in question is preferably a homogeneous mixture.

The constituent particles of the initial mixture may have a particle size of less than 4 mm, preferably less than 1.5 mm.

The aqueous solution may be between 40% and 75% by total weight of the mixture. The proportion of water may be adjusted to obtain a viscosity of the final bone paste that is suitable for requirements. A reduced water content of 40% will give a higher viscosity, providing a putty consistency. An increased water content of up to 75% will give a lower viscosity, providing a gel consistency. This is valid for all embodiments of the invention.

The aqueous solution of the initial mixture may be chosen from among water, normal saline (sodium chloride solution, for example 0.9%), or a physiological buffer solution of phosphate or the like.

The granular product of the initial mixture may possibly further comprise a mineralized osteoconductive biomaterial; this osteoconductive biomaterial may be of human or animal origin (deproteinized bone matrix) or synthetic (hydroxyapatite, tricalcium phosphate, bioglass, or other implantable material). The mineralized biomaterial may have a particle size of less than 4 mm, preferably less than 1.5 mm. The proportion of mineralized biomaterial possibly added to the initial mixture may represent between 10% and 40% of the initial mixture by dry weight. More generally, the proportion of added osteoconductive biomaterial may be adjusted to maintain the properties of malleability and cohesion of the final bone paste.

Several examples of the preparation of the initial mixture are detailed below.

1. Case where the Initial Mixture Comprises Mineralized Bone Matrix Particles and Demineralized Bone Matrix Particles:

When the initial mixture comprises mineralized bone matrix particles and completely demineralized bone matrix particles, step (a) of providing the initial mixture may comprise at least the following sub-steps:
(a1) a sub-step of preparing completely demineralized bone matrix particles by demineralization and grinding of bone fragments (the demineralization preceding or following the grinding);
(a2) a sub-step of preparing mineralized bone matrix particles by grinding bone fragments;
(a3) a sub-step of mixing during which the completely demineralized bone matrix particles, the mineralized bone matrix particles, and the aqueous solution are mixed to obtain said initial mixture.

2. Case where the Initial Mixture Comprises Partially Demineralized Bone Matrix Particles:

When the initial mixture comprises partially demineralized bone matrix particles, step (a) of providing the initial mixture may comprise at least the following sub-steps:
(a'1) a sub-step of preparing partially demineralized bone matrix particles by demineralization and grinding of bone fragments (the demineralization preceding or following the grinding);
(a'3) a sub-step of mixing during which the partially demineralized bone matrix particles and the aqueous solution are mixed to obtain said mixture.

3. Case where the Initial Mixture Comprises Collagen Particles and Particles of Mineralized Bone Matrix:

When the initial mixture comprises purified collagen particles and mineralized bone matrix particles, step (a) of providing the initial mixture may comprise at least the following sub-steps:
(a"1) a sub-step of preparing purified collagen particles by any technique for obtaining a dehydrated purified collagen,
(a"2) a sub-step of preparing mineralized bone matrix particles by grinding bone fragments,
(a"3) a sub-step of mixing during which at least the bone matrix particles, the purified collagen particles, and the aqueous solution are mixed to obtain said initial mixture.

It is possible during the mixing sub-step (a3, a'3, or a"3) to mix a mineralized osteoconductive biomaterial with the other constituents of the initial mixture.

(b) Heating Step:

During the heating step, the initial mixture is heated sufficiently to transform a portion of the collagen into gelatin and thus obtain the desired bone paste, which is homogeneous and ready for use after cooling and gelling.

During this heating step, the initial mixture may be heated for a period of between 10 minutes and 2 hours, preferably between 18 min and 1 hour.

The initial mixture may be heated at a temperature of between 50° C. and 200° C., preferably between 100° C. and 150° C.

More particularly, the initial mixture may advantageously be heated for a period of between 18 min and 1 hour and at a temperature of between 100° C. and 150° C. In particular, the initial mixture may advantageously be heated for a period of about 30 minutes to 1 hour (30 minutes in case 1 above, or 1 hour in case 2 above) at a temperature of about 120° C. (for example 121° C.).

More generally, the heating step (b) is advantageously carried out at a sufficient temperature and for a sufficient period of time to sterilize the bone paste.

The heating may be carried out in water vapor, a water bath, or dry heat.

Advantageously, at the end of the providing step (a), the initial mixture is placed in a fluidtight container that is resistant to heat and pressure differences due to the heating system used (of course, the container in the closed state is fluidtight to water vapor so that pressure differences can exist between inside and outside the container; for example, the container can withstand pressure differences of at least 1 bar when using an autoclave at 121° C.), and it is heated in the heating step (b) in said fluidtight container, such that a sterile bone paste is obtained that is ready for use after cooling, with no additional step of sterilization or of packaging in another container. The container 1 in question may be, for example, a vial 2 such as the one represented in FIG. 1, of glass or other material that can withstand the required temperature, closed with a cap 3 screwed or fitted into place, and containing the bone paste 4. As is clearly visible in FIG. 1, here the cap 3 covers a single opening of the vial 2. Of course, the fluidtight and closed state of the container may be obtained during the heating step (b) or immediately thereafter, as appropriate. Although FIG. 1 shows a container in two parts, consisting of a vial 2 and a cap 3, this is in no way limiting. The container may also correspond to the use of an assembly of one or more non-rigid envelopes, an assembly of at least two or three parts, and/or a portion with several closure elements.

Advantageously, at the end of step (a) the container may be placed in a sealed double bag that is permeable to gas only, so that the packaging is complete prior to the heating step (b). this allows keeping the containing vial 1 and the bone paste 4 in a sterile state until use in the operating room (as the container not opened until that point).

No end sterilization by gamma or beta irradiation (harmful to gelatin integrity) is required.

Figure 2:
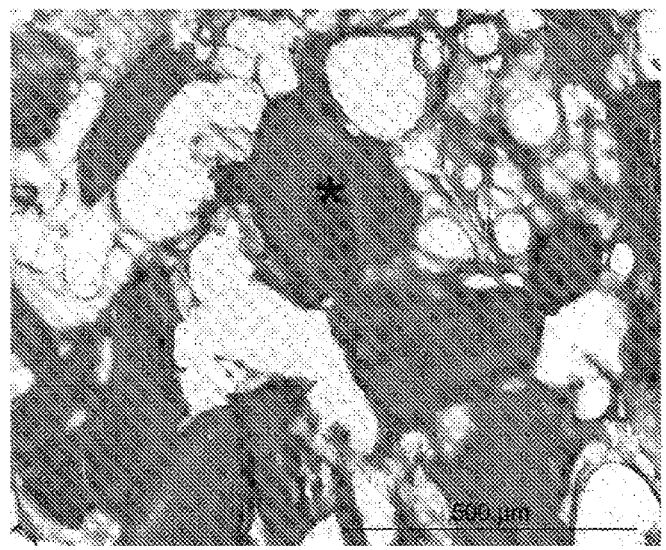
FIG. 2 is a photograph showing the appearance of bone paste resulting from the method according to the preferred method of preparation.
Figure 3:
FIG. 3 is a photograph showing the appearance of untreated particles of bone powder, before the method is implemented.

A mixing operation is carried out in the providing step (a), with a liquid portion and a solid portion composed of at least partially mineralized bone matrix particles containing collagen. Such particles may be obtained in a (prior) sub-step of partial demineralization. In FIG. 2, a photo captured with a Leica® DM2000 microscope connected to a digital camera (controlled by image acquisition software) illustrates the result of the method, after the heating step (b). One can see that the partially demineralized particles (here all the particles in the case of FIG. 2) have a central mineralized portion and a peripheral demineralized portion. Between the particles, a gel phase has formed by exudation of gelatin from the collagen of the particles, due to the specific heat treatment exceeding 100° C. This helps to better combine the phases of the bone paste 4. For comparison, untreated bone powder (prior to treatment by the method, without demineralization treatment) is represented in FIG. 3. Each particle has a homogeneous composition, and the obvious absence of gel between the particles means that the corresponding powder does not have the rheological properties of a paste (not malleable, non-cohesive, and non-injectable).

Several examples are detailed below.

EXAMPLE 1

Case where an Initial Mixture of Demineralized Bone Matrix and Mineralized Bone Matrix is Used (a1) Preparation of Completely Demineralized Bone Matrix Particles:

A cortical-cancellous bone fragment is ground to powder form, the particle size preferably being less than 1.5 mm, the particles in question including fines (particle size <0.2 mm in this specific case).

Next, the bone matrix particles are completely demineralized by two successive baths in 0.5 N hydrochloric acid at room temperature for 4 h while stirring, using 50 ml hydrochloric acid per gram of bone matrix (thus removing 100% of the minerals from the mineral fraction). This is neutralized with a solution of 1N sodium hydroxide to bring the pH to 7, then rinsed with water and dried under a stream of hot air for 15 h.

(a2) Preparation of Mineralized Bone Matrix Particles:

A mineralized cortical-cancellous bone fragment is ground to powder form, the particle size preferably being less than 1 mm in order to form the mineralized bone matrix.

(a3) Mixing:

The completely demineralized bone matrix particles, the mineralized bone matrix particles, and the water are mixed. The proportions by weight of the total mixture may be, for example, demineralized bone matrix: 10%; mineralized bone matrix: 25%; water: 65%.

(b) Heating:

The container holding the mixture is heated by autoclaving, at 121° C. for 30 min.

In this type of configuration, heating transforms a major portion of the demineralized bone matrix particles and a portion of the collagen of the mineralized bone matrix particles into gelatin, which obtains a material continuity between the gel phase (gelatin) and the solid phase (mineralized bone matrix particles). After cooling and gelling, the bone paste is sterile and ready for use and has the viscosity of putty.

EXAMPLE 2

Case where an Initial Mixture of Partially Demineralized Bone Matrix is Used, Without Added Mineralized Bone Matrix (a'1) Preparation of Partially Demineralized Bone Matrix Particles:

A cortical-cancellous bone fragment is ground to powder form, the particle size preferably being less than 1.5 mm, the particles in question including fines (particle size <0.2 mm in this specific case).

The bone matrix particles are then partially demineralized in 0.4 N hydrochloric acid at room temperature for 1 h or 1:30 h while stirring, using 10 ml hydrochloric acid per gram of bone matrix (thus removing 50% of the minerals from the mineral fraction). This is neutralized with a solution of 1N sodium hydroxide to bring the pH to 7, then rinsed with water and dried under a stream of hot air for 15 h.

(a'3) Mixing:

The partially demineralized bone matrix particles and the water are mixed in a fluidtight container. The proportions by weight of the total mixture may be, for example: partially demineralized bone matrix particles 35%; water: 65%.

(b) Heating:

The fluidtight container holding the mixture is heated by autoclaving, at 121° C. for 1 hour.

In this type of configuration, heating transforms a portion of the collagen of the partially demineralized bone matrix particles into gelatin, which obtains material continuity between the gel phase (gelatin) and the solid phase (remaining portion of the partially demineralized bone matrix particles). After cooling and gelling, the bone paste is sterile and ready for use.

With the above-mentioned water content of 65%, the bone paste has the consistency of liquid gel. The viscosity of the final bone paste can be adjusted to requirements, by changing the proportion of water in the initial mixture. For example, a water content of 55% will give a higher viscosity, while remaining injectable by a syringe with an approximately 3 mm diameter opening. This observation is valid for all embodiments of the invention.

EXAMPLE 3

Case where an Initial Mixture of Collagen and Mineralized Bone Matrix is Used (a"1) Preparation of Collagen Particles:
Collagen is selected that is in powder or filament form, dehydrated by lyophilization or any other drying method.

(a"2) Preparation of Mineralized Bone Matrix Particles:
A mineralized cortical-cancellous bone fragment is ground to powder form, the particle size preferably being less than 1 mm, in order to form the mineralized bone matrix.

(a"3) Mixing:
The collagen particles, mineralized bone matrix particles, and water are mixed. The proportions by weight of the total mixture may be, for example: collagen: 10%; mineralized bone matrix: 25%; water: 65%.

(b) Heating:
The container holding the mixture is heated by autoclaving, at 121° C. for 30 min.

Heating transforms a major portion of the pure collagen and a portion of the collagen of the mineralized bone matrix particles into gelatin, which obtains material continuity between the gel phase (gelatin) and the solid phase (mineralized bone matrix particles). After cooling and gelling, the bone paste is sterile and ready for use and has the viscosity of a paste.

EXAMPLE 4

Case where an Initial Mixture of Partially Demineralized Bone Matrix and a Mineralized Osteoconductive Biomaterial is Used (a1) Preparation of Partially Demineralized Bone Matrix Particles:
A cortical-cancellous bone fragment is ground to powder form, the particle size preferably being less than 1.5 mm, the particles in question including fines (particle size <0.2 mm in this specific case).

The bone matrix particles are then partially demineralized in 0.6 N hydrochloric acid at room temperature for 1 hour while stirring, using 10 ml hydrochloric acid per gram of bone matrix (thus removing 70% of the minerals from the mineral fraction). This is neutralized with a solution of 1N sodium hydroxide to bring the pH to 7, then rinsed with water and dried under a stream of hot air for 15 h.

(a'2) Providing a Mineralized Osteoconductive Biomaterial:
The osteoconductive biomaterial is selected from among synthetic biomaterials in powder form such as beta-tricalcium phosphate. The particle size of the biomaterial powder is preferably between 0.2 mm and 1 mm.

(a'3) Mixing:
The partially demineralized bone matrix particles, the beta-tricalcium phosphate powder, and the water are mixed in a fluidtight container. The proportions by weight of the total mixture may be, for example: partially demineralized bone matrix particles: 30%; beta-tricalcium phosphate particles: 10%; water: 60%.

(b) Heating:
The fluidtight container holding the mixture is heated by autoclaving, at 121° C. for 45 min. After cooling and gelling, the bone paste is sterile and ready to use and has the viscosity of putty.

The invention claimed is:

1. A method for preparing an osteoconductive bone paste, comprising the following steps:
   (a) a providing step during which an initial mixture is supplied, in a container, the initial mixture including an aqueous solution and a granular product comprising at least collagen and minerals, the collagen representing between 30 and 90% of the granular product by dry weight and the minerals representing between 10 and 70% of the granular product by dry weight, at least a portion of the collagen being contained in particles of at least partially mineralized bone matrix,
   (b) a heating step during which the initial mixture is heated in the container, at a temperature of at least 100° C., to transform a portion of the collagen into gelatin so that there is continuity between the gelatin and the at least partially mineralized bone matrix and a cohesive bone paste is thus obtained of defined viscosity, the heating step enabling sterilization of the bone paste in the container,
   the bone paste being kept in the container, so that after cooling and gelling, the bone paste is ready for use and remains sterile in said container, the container being in a closed and fluidtight state.

2. The method according to claim 1, wherein, in the heating step (b), the initial mixture is heated for a period of between 10 minutes and 2 hours.

3. The method according to claim 1, wherein, in the heating step (b), the initial mixture is heated for a period of between 18 minutes and 1 hour and at a temperature of between 100° C. and 150° C.

4. The method according to claim 1, wherein, in the providing step (a), the initial mixture:
   is supplied in the container in a closed and fluidtight state, and
   is heated in the heating step (b) in said container in this closed and fluidtight state.

5. The method according to claim 4, wherein, in the providing step (a), the fluidtight container is placed in a sealed pouch and is heated in the heating step (b) in said sealed pouch.

6. The method according to claim 1, wherein the heating step (b) is carried out in water vapor, a water bath, or dry heat.

7. The method according to claim 1, wherein, in the providing step (a), the minerals represent between 20% and 60% by dry weight of the granular product and the collagen represents between 40% and 80% by dry weight of the granular product.

8. The method according to claim 1, wherein, in the providing step (a), the aqueous solution of the initial mixture is selected from among water, normal saline, or a physiological buffer solution.

9. The method according to claim 1, wherein, in the providing step (a), the aqueous solution represents between 40% and 75% of the initial mixture by total weight.

10. The method according to claim 1, wherein, in the providing step (a), the granular product has a particle size of less than 4 mm.

11. The method according to claim 1, wherein, in the providing step (a), the initial mixture further contains a mineralized osteoconductive biomaterial.

12. The method according to claim 1, wherein, in the providing step (a), the initial mixture contains completely demineralized bone matrix particles and mineralized bone matrix particles.

13. The method according to claim 1, wherein, in the providing step (a), the initial mixture contains partially demineralized bone matrix particles comprising between 20% and 70% minerals by dry weight.

14. The method according to claim 1, wherein, in the providing step (a), the initial mixture comprises purified collagen and mineralized bone matrix particles.

15. The method according to claim 12, wherein the providing step (a) comprises at least the following sub-steps:
   (a1) a sub-step of preparing completely demineralized bone matrix particles by demineralization and grinding of bone,
   (a2) a sub-step of preparing mineralized bone matrix particles by grinding bone,
   (a3) a sub-step of mixing during which at least the completely demineralized bone matrix particles, the mineralized bone matrix particles, and the aqueous solution are mixed to obtain said initial mixture.

16. The method according to claim 13, wherein the providing step (a) comprises at least the following sub-steps:
   (a'1) a sub-step of preparing partially demineralized bone matrix particles by demineralization and grinding of bone,
   (a'3) a sub-step of mixing during which at least the partially demineralized bone matrix particles and the aqueous solution are mixed to obtain said initial mixture.

17. The method according to claim 14, wherein the providing step (a) comprises at least the following sub-steps:
   (a"2) a sub-step of preparing mineralized bone matrix particles by grinding bone,
   (a"3) a sub-step of mixing during which at least the mineralized bone matrix particles, the purified collagen, and the aqueous solution are mixed to obtain said initial mixture.

18. The method according to claim 15, wherein, during the mixing sub-step, at least one mineralized osteoconductive biomaterial is mixed with the other constituents of the initial mixture.

19. The method according to claim 16, wherein, during the mixing sub-step, at least one mineralized osteoconductive biomaterial is mixed with the other constituents of the initial mixture.

20. The method according to claim 17, wherein, during the mixing sub-step, at least one mineralized osteoconductive biomaterial is mixed with the other constituents of the initial mixture.

21. A method for preparing an osteoconductive bone paste, comprising:
   supplying an initial mixture in a container, the initial mixture including an aqueous solution and a granular product comprising at least collagen and minerals, the collagen representing between 30 and 90% of the granular product by dry weight and the minerals representing between 10 and 70% of the granular product by dry weight, at least a portion of the collagen being contained in particles of at least partially mineralized bone matrix, aqueous solution being mixed with the granular product to obtain the initial mixture,
   heating the initial mixture in the container, at a temperature of at least 100° C., to transform a portion of the collagen into gelatin so that there is continuity between the gelatin and the at least partially mineralized bone matrix and a cohesive bone paste of defined viscosity is directly obtained from the initial mixture, the bone paste being sterilized in the container due to the heating of the initial mixture, the bone paste being kept in the container, so that, after cooling and gelling, the bone paste is ready for use and remains sterile in the container, the container being in a closed and fluidtight state.

22. The method of claim 21, wherein the initial mixture is heated in the container, which is a vial made of glass, so that the following parts of the mixture are simultaneously heated in a common interior volume of the container:
   the granular product that includes the particles of at least partially mineralized bone matrix, and
   the aqueous solution that represents between 40% and 75% of the initial mixture by total weight before the heating.

\* \* \* \* \*